United States Patent
Howard et al.

(10) Patent No.: US 7,901,553 B2
(45) Date of Patent: Mar. 8, 2011

(54) METHOD AND SYSTEM FOR SENSING GAS INCORPORATING AN INTEGRATED REFERENCE ELEMENT

(75) Inventors: Timothy Howard, Canyon Country, CA (US); Carlton Salter, Stevenson Ranch, CA (US)

(73) Assignee: H2scan Corporation, Valencia, CA (US)

( * ) Notice: Subject to any disclaimer, the term of this patent is extended or adjusted under 35 U.S.C. 154(b) by 864 days.

(21) Appl. No.: 11/046,398

(22) Filed: Jan. 27, 2005

(65) Prior Publication Data

US 2005/0189238 A1  Sep. 1, 2005

Related U.S. Application Data

(60) Provisional application No. 60/540,021, filed on Jan. 27, 2004.

(51) Int. Cl.
*G01N 27/26* (2006.01)
(52) U.S. Cl. ......... 204/400; 257/253; 257/288; 257/213; 257/202; 257/207; 73/31.06; 204/431; 324/71.5
(58) Field of Classification Search .......... 257/202–207, 257/213, 288, 253; 204/400, 431; 73/31.06; 324/71.5
See application file for complete search history.

(56) References Cited

U.S. PATENT DOCUMENTS

| | | | |
|---|---|---|---|
| 4,058,368 A | 11/1977 | Svensson et al. | |
| 4,650,561 A * | 3/1987 | Robins et al. | 204/416 |
| 5,011,589 A | 4/1991 | Amemiya et al. | |
| 5,235,267 A * | 8/1993 | Schoneberg et al. | 324/71.5 |
| 5,279,795 A | 1/1994 | Hughes et al. | |
| 5,367,283 A * | 11/1994 | Lauf et al. | 338/34 |
| 6,120,835 A * | 9/2000 | Perdieu | 427/125 |
| 6,458,327 B1 * | 10/2002 | Vossmeyer | 422/68.1 |

FOREIGN PATENT DOCUMENTS

| | | |
|---|---|---|
| WO | WO-03/050526 A | 6/2003 |
| WO | WO 03/050526 A1 | 6/2003 |

OTHER PUBLICATIONS

T. L. Poteat, B. Lalevic, Transition Metal-Gate MOS Gaseous Detectors, 1982, IEEE Transactions on Electron Devices, 29, pp. 123-129.*
Hughes, Robert C. et al., "Sensors for Detecting Molecular Hydrogen Based on Pd Metal Alloys", Sandia National Laboratories, Microsensor Research and Development Department, Albuquerque, NM, 1997.
W L Gore & Associates, "GORE™ Membrane Vents, Series HPM: High Protection Against Metal Impact" Product Data Sheet, 2002.

* cited by examiner

*Primary Examiner* — Nam X Nguyen
*Assistant Examiner* — Bach T Dinh
(74) *Attorney, Agent, or Firm* — McAndrews, Held & Malloy, Ltd.

(57) ABSTRACT

A system for sensing a gas stream constituent comprises: (a) a thermally conductive, electrically insulative substrate, (b) a gas-sensing element mounted on the substrate and capable of sensing the constituent, (c) a reference element mounted on the substrate having electrical properties congruent with the gas-sensing element and being insensitive to the constituent, (d) an electronic circuit interconnecting the gas-sensing element and the reference element. The circuit is capable of actuating both of the elements and measuring the voltage difference between the elements. The voltage difference is proportional to the concentration of the constituent in the gas stream.

12 Claims, 3 Drawing Sheets

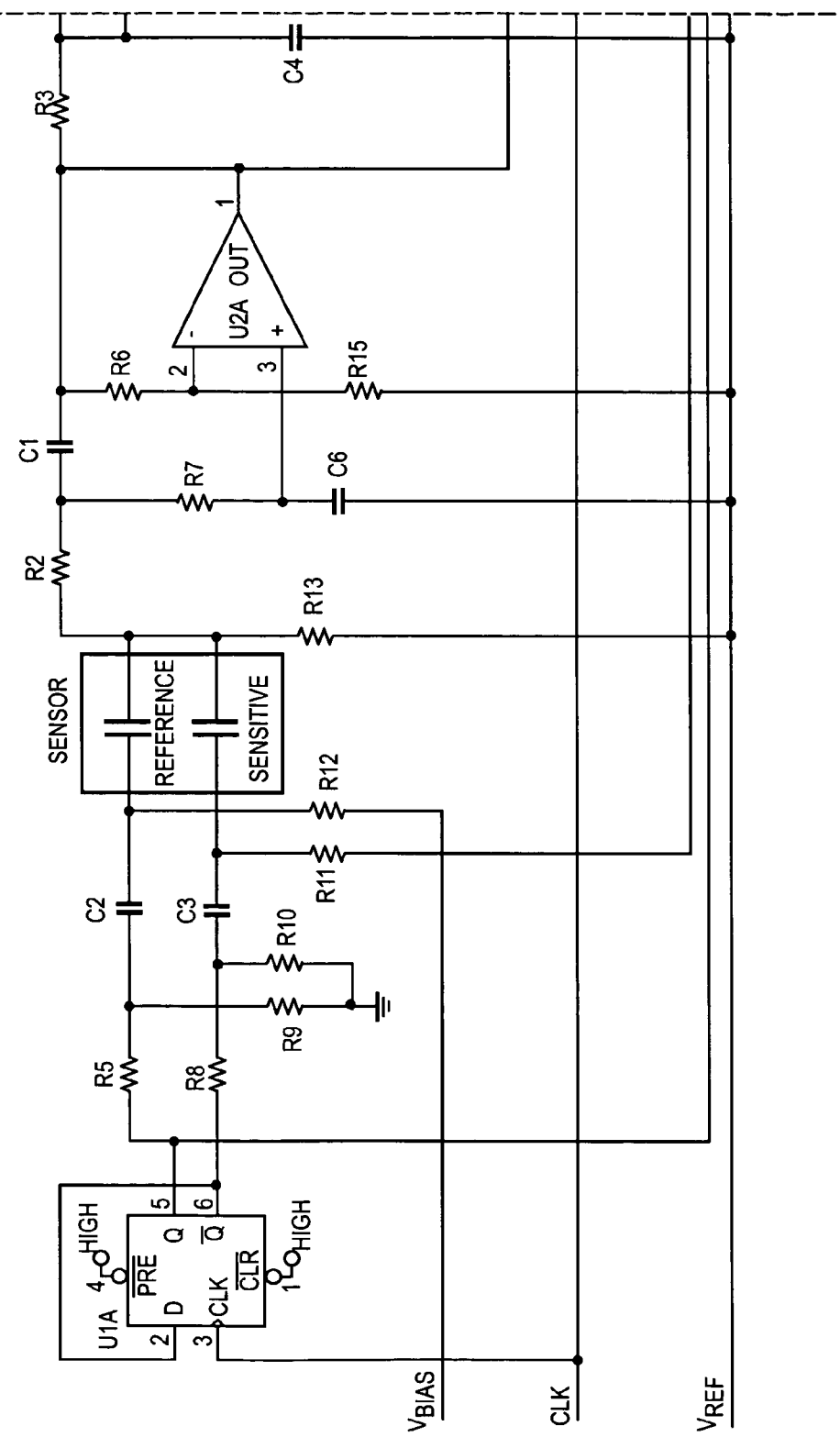

METHOD AND SYSTEM FOR SENSING GAS INCORPORATING AN INTEGRATED REFERENCE ELEMENT

CROSS-REFERENCE TO RELATED APPLICATIONS(S)

This application is related to and claims priority benefits from U.S. Provisional Patent Application Ser. No. 60/540,021, filed on Jan. 27, 2004. The '021 provisional application is hereby incorporated by reference herein in its entirety.

FIELD OF THE INVENTION

The present invention relates to sensors for detecting the presence of a constituent in a gaseous stream. More particularly, the present invention relates to a hydrogen gas sensor configuration and electronic circuitry for monitoring and measuring a constituent of a gas stream.

BACKGROUND OF THE INVENTION

Several factors affect the overall accuracy of a gas sensor system: temperature, voltage, drift, frequency and noise are a few of the primary factors. The objective in designing gas sensor systems is to reduce or eliminate the effects of these factors on the accuracy of the gas sensor.

Typically this objective is achieved by tightening the tolerances of the electronic components employed in the detection circuit. Alternatively, a bridge circuit is used with a precision reference element.

The cost of precision components has a negative impact on the design. In addition, devices of high enough precision may not be available to meet the product requirements.

SUMMARY OF THE INVENTION

The present gas sensor design incorporates a reference element of the same or similar type and geometry as the gas-sensing element on the same substrate. The gas detection circuitry actuates both the gas-sensitive and reference elements and measures the voltage difference between them. The voltage difference is proportional to the gas concentration and is essentially undominated by changes in temperature, voltage, drift, frequency, noise and/or other similar factors.

A system for sensing a gas stream constituent comprises:
(a) a thermally conductive, electrically insulative substrate;
(b) a gas-sensing element mounted on the substrate, the gas-sensing element capable of sensing the constituent;
(c) a reference element mounted on the substrate, the reference element and the gas-sensing element having congruent electrical properties, the reference element insensitive to the constituent;
(d) an electronic circuit interconnecting the gas-sensing element and the reference element, the circuit capable of actuating both of the elements and measuring the voltage difference between the elements.

In operation, the voltage difference is proportional to the concentration of the constituent in the gas stream In a preferred system, the gas stream constituent is hydrogen.

In a preferred system, each of the gas-sensing element and the reference element comprises a material having electrical properties that change upon exposure to the gas stream constituent. Each of the gas-sensing element and the reference element can be a metal-gated metal-oxide semiconductor (MOS) solid-state device. The MOS device can be a MOS capacitor or a MOS transistor.

The metal gate of the gas-sensing MOS device preferably comprises a metal selected from the group consisting of palladium and a palladium alloy. The palladium alloy is preferably selected from the group consisting of palladium/nickel, palladium/gold and palladium/silver.

The metal gate of the reference element MOS device preferably comprises a metal that is inert with respect to the gas stream constituent. The preferred inert metal is gold.

The metal gate of the reference element MOS device can also comprise a passivated metal that is non-inert with respect to the gas stream constituent. The non-inert metal is preferably passivated by application of an inert coating material.

In a preferred system, the substrate comprises a silicon-containing material.

The gas-sensing element and the reference element can also be selected from the group consisting of transistors and diodes. The transistors can be selected from the group consisting of p-n-p transistors and field effect transistors.

A method for sensing a gas stream constituent comprises:
(a) mounting a gas-sensing element on a thermally conductive, electrically insulative substrate, the gas-sensing element capable of sensing the constituent;
(b) mounting a reference element on the substrate, the reference element and the gas-sensing element having congruent electrical properties, the reference element insensitive to the constituent having essentially the same composition and conformation as the constituent-sensitive element;
(c) interconnecting the gas-sensing element and the reference element in an electronic circuit;
(d) actuating both of the gas-sensing element and the reference element through the electronic circuit; and
(e) measuring the voltage difference between the gas-sensing element and the reference element through the electronic circuit, the voltage difference being proportional to the concentration of the gas stream constituent.

BRIEF DESCRIPTION OF THE DRAWING(S)

DETAILED DESCRIPTION OF PREFERRED EMBODIMENT(S)

Figure 1:
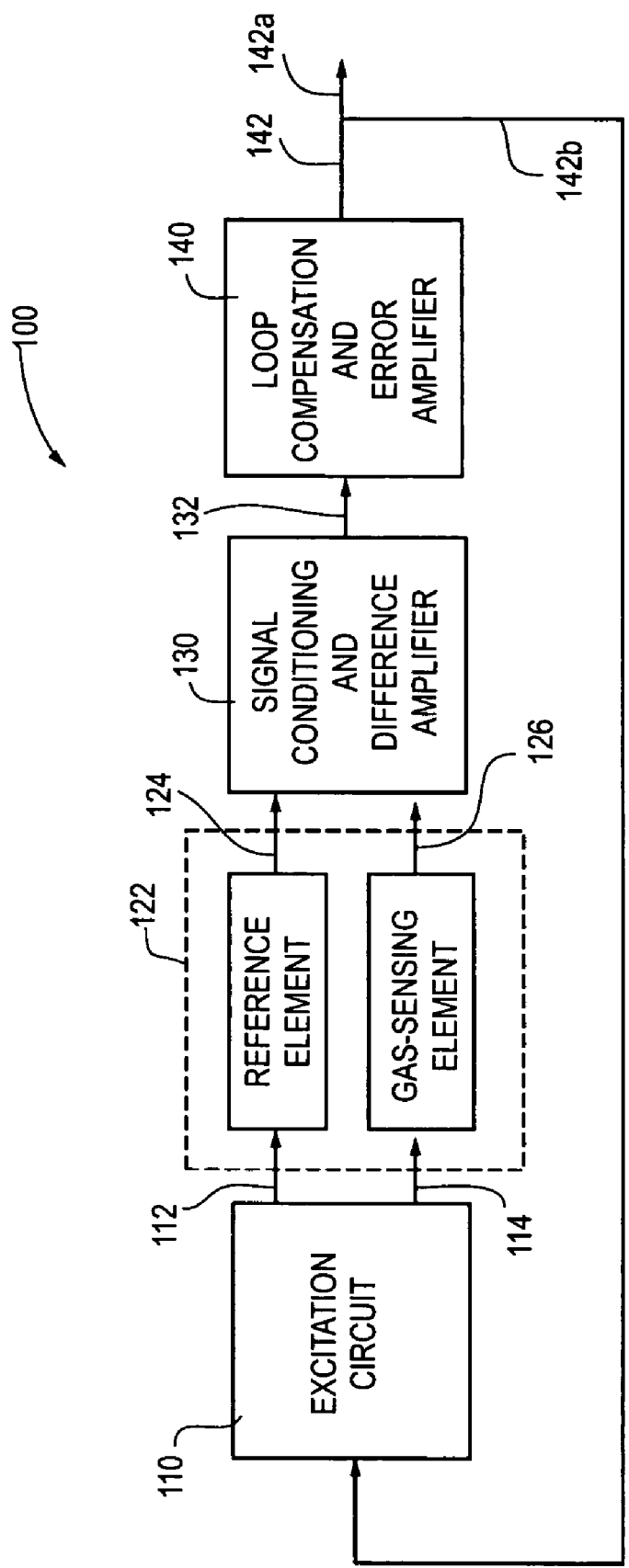
FIG. 1 is a schematic flow diagram of the functions implemented in the electronic circuitry for the present gas sensing system incorporating an integrated reference element.

Turning to FIG. 1, an embodiment of the gas-sensing system circuitry employs the illustrated functions to sense and measure the concentration of hydrogen in a gas stream using a reference element. An excitation circuit 110 generates electrical signals 112, 114 to actuate the gas-sensing element and reference element depicted in sensor 122. A feedback signal 142b input to excitation circuit 110 adjusts signal 114 to gas-sensing element such that the output from the gas-sensing element of sensor 122 is equal to that of the reference element. There are also programmable adjustments for the reference element that establish the input signal to the reference element. The output 124, 126 from the reference and gas-sensing elements, respectively, are inputs to signal conditioning and difference amplifier section 130. Signal conditioning includes noise filtering and conversion or scaling of the signals as required for the error amplifier. Loop compensation and error amplifier section 140 provides additional signal processing for loop stability. Output signal 142 is proportional to the gas stream constituent concentration, and is fed back via signal 142b to excitation circuit 110 and on to other electronic components via signal 142a for reporting a calibrated output from sensor 122.

Figure 2B:
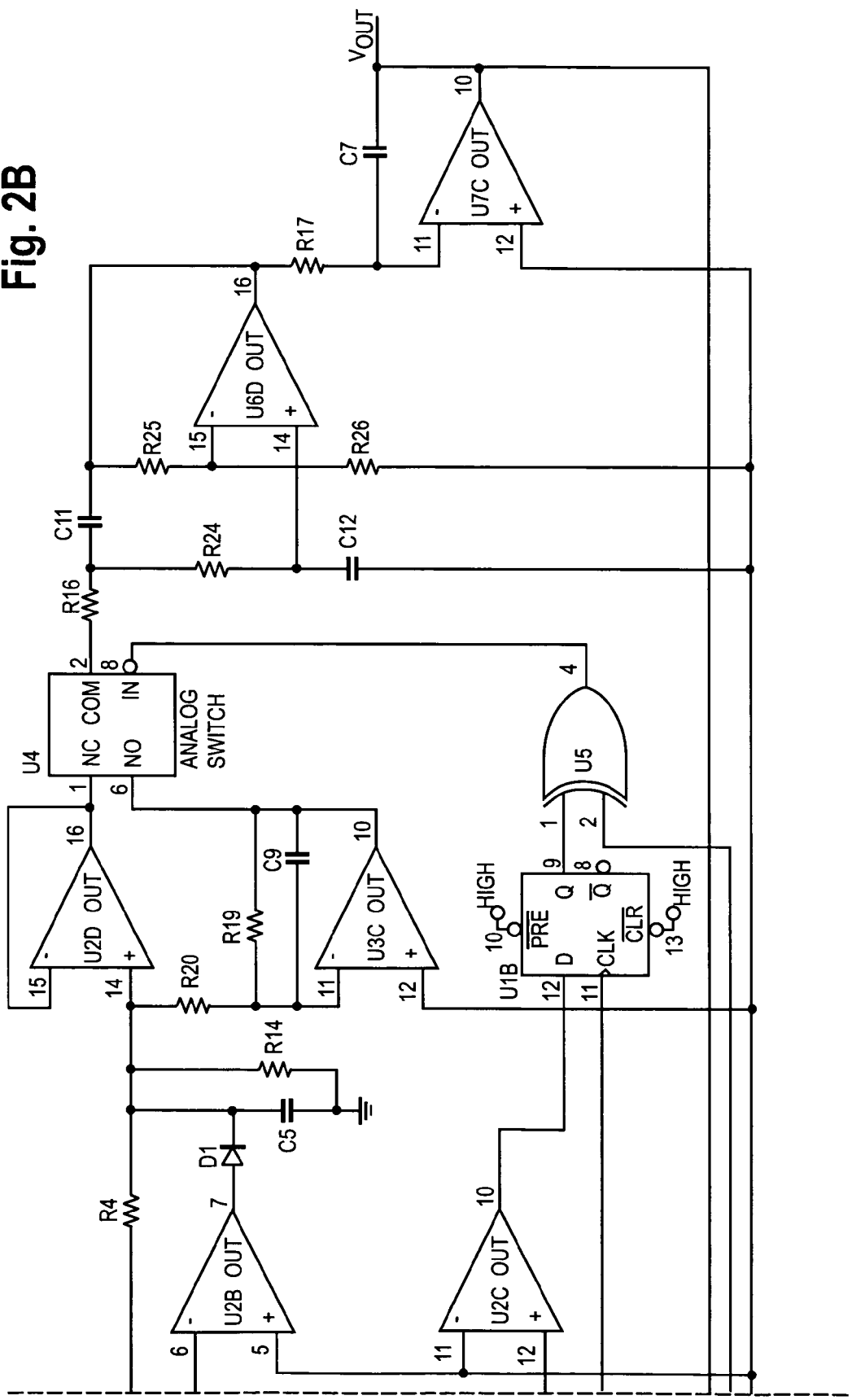
FIG. 2 is a detailed circuit diagram of the present gas sensing system incorporating an integrated reference element.

FIG. 2 is a detailed circuit diagram of the present gas sensing system incorporating an integrated reference element.

The present gas-sensing system can also include other elements such as a heater and temperature-sensing device to keep the sensor at a constant temperature. Other gas-sensing elements, such as for example resistors, diodes and/or other transistor or semiconductor devices, can also be present and may or may not have corresponding reference elements associated with them. The present reference element is preferably made with the same processes, materials and configuration as the gas-sensing element except it is made essentially insensitive to the gas. The reference element is thus affected by temperature, voltage, drift, frequency, noise and other factors to essentially the same degree as the gas-sensing element. The difference between the reference and gas-sensing elements is predominately a function of the gas concentration.

In a preferred system embodiment, the precision reference element is placed on the same substrate as the gas-sensing element. Conventional, prior art solutions did not include an integrated reference element.

The preferred reference element is made essentially insensitive to hydrogen gas by using a metal that is essentially insensitive to hydrogen (for example, gold) rather than palladium-nickel in a metallization step. The reference element could also be a material that, although at least somewhat sensitive to hydrogen, has been desensitized by using a coating ($SiO_2$ for example) that prevents hydrogen from reaching the reference metal.

The gas-sensitive and reference elements are preferably metal-on-silicon (MOS) capacitors. The MOS devices are not restricted to a capacitive form, however, but could be in p-n-p transistor, field-effect transistor (FET) or diode configurations as well.

The gas detection circuitry adjusts the bias voltage of the gas-sensitive capacitor to match the capacitance of the reference capacitor.

The change in bias voltage on the gas-sensitive capacitor is proportional to gas concentration. Conventional, prior art solutions measured capacitance.

The present gas detection circuit drives the reference and gas-sensitive capacitors with complimentary square wave (or other alternating current (AC) wave forms) signals that cancel when added together. The control loop drives the bias voltage of the gas-sensitive capacitor to maintain a minimum amplitude for the sum of the outputs.

Other embodiments of the present device may not employ a bias voltage to minimize the sum of the outputs, but could simply measure the difference voltage.

The solution described here has been built and tested for sensing hydrogen gas. Preferred embodiments of the gas-sensitive and reference elements are implemented as MOS capacitors. Tests of the gas detection circuitry with the present hydrogen sensing capacitor have shown that the device is capable of detecting hydrogen concentrations below 10 parts per million (ppm). Tests have also shown that the sensor performs favorably over changes in temperature, voltage, frequency and noise.

Although the present device has been implemented in its preferred embodiment to sense hydrogen, persons skilled in the technology involved here will recognize that one or more aspects of the present device could be implemented or readily modified to sense and/or detect the presence and/or amount of constituents in fluid streams generally, including gas streams containing hydrogen and/or other than hydrogen, liquid streams, liquid streams containing entrained gas(es) and/or solid(s), gas streams containing entrained liquid(s) and/or solid(s). Moreover, aspects of the present device could be implemented or readily modified to sense and/or detect the presence and/or amount of fluid constituents residing in the pores and/or lattice structure of solids.

The present solution provides lower overall cost than conventional, prior art solutions since lower precision components can be employed to achieve the same or similar overall accuracy of the sensor system.

The present solution provides overall higher accuracy in comparison to conventional, prior art gas sensing devices, since the precision reference element matches the characteristics of the gas-sensing element.

While particular steps, elements, embodiments and applications of the present invention have been shown and described, it will be understood, of course, that the invention is not limited thereto since modifications can be made by those skilled in the art, particularly in light of the foregoing teachings.

What is claimed is:

1. A system for sensing hydrogen in a gas stream, the system comprising:
   (a) a thermally conductive, electrically insulative substrate;
   (b) a metal-gated metal-oxide semiconductor (MOS) gas-sensing element mounted on said substrate, said MOS gas-sensing element comprising a MOS gas sensing capacitor having a capacitance at a bias voltage, said MOS gas-sensing element capable of sensing said hydrogen in said gas stream;
   (c) a metal-gated metal-oxide semiconductor (MOS) reference element mounted on said substrate, said MOS reference element comprising a MOS reference capacitor having a capacitance, said metal-gate comprising a metal that is inert with respect to said hydrogen in said gas stream, said MOS reference element and said MOS gas-sensing element having congruent electrical properties; and
   (d) an electronic circuit interconnecting said MOS gas-sensing element and said MOS reference element, said circuit capable of actuating both of said elements, adjusting the bias voltage of said MOS gas-sensing capacitor to match the capacitance of said MOS gas-sensing capacitor with the capacitance of said MOS reference capacitor and driving said MOS reference capacitor and said MOS gas-sensing capacitor with complimentary AC waveforms signals that cancel when added together and having a control loop which drives the bias voltage of said MOS gas-sensing capacitor to maintain a minimum amplitude for a sum of outputs;
   whereby a concentration of hydrogen in said gas stream has a proportional relationship to a change in the bias voltage.

2. The system of claim 1 wherein said MOS gas-sensing element comprises a material having electrical properties that change upon exposure to said hydrogen in said gas stream.

3. The system of claim 1 wherein the metal gate of said MOS gas-sensing element comprises a metal selected from the group consisting of palladium and a palladium alloy.

4. The system of claim 3 wherein said palladium alloy is selected from the group consisting of palladium/nickel, palladium/gold and palladium/silver.

5. The system of claim 1 wherein said inert metal is gold.

6. The system of claim 1 wherein said substrate comprises a silicon-containing material.

7. A method for sensing hydrogen in a gas stream comprising:
   (a) mounting a metal-gated metal-oxide semiconductor (MOS) gas-sensing element on a thermally conductive, electrically insulative substrate, said MOS gas-sensing element comprising a MOS gas-sensing capacitor having a capacitance at a bias voltage, said MOS gas-sensing element capable of sensing said hydrogen in said gas stream;
   (b) mounting a metal-gated metal-oxide semiconductor (MOS) reference element on said substrate, said MOS reference element comprising a MOS reference capacitor having a capacitance, said MOS reference element and said MOS gas-sensing element having congruent electrical properties, said MOS reference element insensitive to said hydrogen in said gas stream having essentially the same composition and conformation as said MOS gas-sensing element;
   (c) interconnecting said MOS gas-sensing element and said MOS reference element in an electronic circuit;
   (d) actuating both of said elements and adjusting the bias voltage on said MOS gas-sensing capacitor to match the capacitance of said MOS gas-sensing capacitor with the capacitance of said MOS reference capacitor and driving said MOS capacitor and said MOS gas-sensing capacitor with complimentary AC waveforms signals that cancel when added together and having a control loop which drives the bias voltage of said MOS gas-sensing capacitor to maintain a minimum amplitude for a sum of outputs, and
   (e) measuring a change in the bias voltage of said electronic circuit, said change in the bias voltage having a proportional relationship to a concentration of said hydrogen in said gas stream.

8. A system for sensing hydrogen in a gas stream, the system comprising:
   (a) a thermally conductive, electrically insulative substrate;
   (b) a metal-gated metal-oxide semiconductor (MOS) gas-sensing element mounted on said substrate, said MOS gas-sensing element comprising a MOS gas-sensing capacitor having a capacitance at a bias voltage, said MOS gas-sensing element capable of sensing said hydrogen in said gas stream;
   (c) a metal-gated metal-oxide semiconductor (MOS) reference element mounted on said substrate, said MOS reference element comprising a MOS reference capacitor having a capacitance, said metal gate comprising a passivated metal that is non-inert with respect to said hydrogen in said gas stream, said MOS reference element and said MOS gas-sensing element having congruent electrical properties; and
   (d) an electronic circuit interconnecting said MOS gas-sensing element and said MOS reference element, said circuit capable of actuating both of said elements and adjusting the bias voltage of said MOS gas-sensing capacitor to match the capacitance of said MOS gas-sensing capacitor with the capacitance of said MOS reference capacitor and driving said MOS gas-sensing capacitor and said MOS reference capacitor with complimentary AC waveforms signals that cancel when added together and having a control loop which drives the bias voltage of said MOS gas-sensing element to maintain a minimum amplitude for a sum of outputs, whereby a concentration of said hydrogen in said gas stream has a proportional relationship to a change in the bias voltage.

9. The system of claim 8 wherein each of said MOS gas-sensing element and said MOS reference element comprises a material having electrical properties that change upon exposure to said hydrogen in said gas stream.

10. The system of claim 8 wherein the metal gate of said MOS gas-sensing element comprises a metal selected from the group consisting of palladium and a palladium alloy.

11. The system of claim 10 wherein said palladium alloy is selected from the group consisting of palladium/nickel, palladium/gold and palladium/silver.

12. The system of claim 8 wherein said substrate comprises a silicon-containing material.

* * * * *